US011304822B2

(12) United States Patent
Prandi et al.

(10) Patent No.: US 11,304,822 B2
(45) Date of Patent: Apr. 19, 2022

(54) DEVICE FOR ASSISTING IN THE PLACEMENT OF A TRAPEZIOMETACARPAL PROSTHESIS

(71) Applicant: Keri Medical SA, Les Acacias (CH)

(72) Inventors: Bernard Prandi, Lucerne (CH); Christian Altheer, Meyrin (CH); Julie Mottet, Pers-Jussy (FR); Eric Maurice, Bordeaux (FR); Joris Duerinckx, Genk (BE)

(73) Assignee: KERI MEDICAL SA, Les Acacias (CH)

( * ) Notice: Subject to any disclaimer, the term of this patent is extended or adjusted under 35 U.S.C. 154(b) by 373 days.

(21) Appl. No.: 16/695,784

(22) Filed: Nov. 26, 2019

(65) Prior Publication Data

US 2020/0163777 A1 May 28, 2020

(30) Foreign Application Priority Data

Nov. 27, 2018 (EP) .................................... 18208586

(51) Int. Cl.
| | |
|---|---|
| *A61F 2/42* | (2006.01) |
| *A61F 2/46* | (2006.01) |
| *A61B 34/10* | (2016.01) |
| *A61F 2/30* | (2006.01) |

(52) U.S. Cl.
CPC ............ *A61F 2/4606* (2013.01); *A61B 34/10* (2016.02); *A61F 2/30942* (2013.01); *A61F 2/4241* (2013.01); *A61B 2034/104* (2016.02); *A61B 2034/105* (2016.02); *A61B 2034/108* (2016.02); *A61F 2002/30952* (2013.01); *A61F 2002/4258* (2013.01); *A61F 2002/4687* (2013.01)

(58) Field of Classification Search
CPC ... A61F 2/42; A61F 2002/4258; A61F 2/4606
See application file for complete search history.

(56) References Cited

U.S. PATENT DOCUMENTS

2009/0254190 A1 10/2009 Gannoe et al.

FOREIGN PATENT DOCUMENTS

| EP | 2564802 A1 | 3/2013 |
|---|---|---|
| WO | 97/42895 A1 | 11/1997 |
| WO | 2014/206498 A1 | 12/2014 |

OTHER PUBLICATIONS

European Search Report issued in European Patent Application No. 18 20 8586 dated May 23, 2019 with English machine translation provided.

*Primary Examiner* — Jason-Dennis N Stewart
(74) *Attorney, Agent, or Firm* — Nixon & Vanderhye

(57) ABSTRACT

Disclosed is a device for assisting in the placement of a trapeziometacarpal prosthesis including a cup to be fixed in the trapezium of a patient and a stem to be fixed in the patient's first metacarpal. The device includes a first guide to be interposed between the trapezium and the first metacarpal, the first guide including a first body having a first surface to be positioned on the articular surface of the trapezium, the first surface congruent with the articular surface of the trapezium and a second surface to face the articular surface of the first metacarpal before resection, the second surface preferably being congruent with the articular surface of the first metacarpal so as to be positionable on the articular surface of the first metacarpal. The first guide also includes locating members carried by the first body and arranged to define resection lines for the first metacarpal.

20 Claims, 2 Drawing Sheets

DEVICE FOR ASSISTING IN THE PLACEMENT OF A TRAPEZIOMETACARPAL PROSTHESIS

BACKGROUND OF THE INVENTION

Field of the Invention

The present invention relates to a device for assisting in the placement of a trapeziometacarpal prosthesis. The present invention also relates to a method of producing such an assistance device.

Description of the Related Art

A trapeziometacarpal prosthesis is indicated for patients suffering from root arthritis and permits replacement of the joint at the base of the thumb by an artificial joint. It is essentially composed of two parts, i.e. a cup intended to be fixed in the patient's trapezium and a stem intended to be fixed in the patient's first metacarpal. An insert is mounted at the end of the stem, generally by means of a collar, and cooperates with the cup to reproduce the trapeziometacarpal joint.

In contrast to prostheses provided for the knee, a trapeziometacarpal prosthesis is difficult to place. In fact, during an operation on a knee, the whole joint between the femur and the tibia is fully visible and accessible and so it is easy to position the various guides and instruments required for the placement of the knee prosthesis. In contrast, the joint between the thumb and the first metacarpal is difficult to access, only very slight spacing between the thumb and the first metacarpal being possible. Furthermore, during an operation at the base of the thumb, the incision made is as small as possible in order not to be too invasive. It is therefore difficult for the surgeon to find the correct angle to position his various guides or tools, such as a guide pin. Furthermore, the distal articular surface of the trapezium is saddle-shaped, concave in the frontal plane and convex in the sagittal plane, and so it is difficult for the surgeon to find a planar surface to be able to position the cup correctly.

Some cup guides have been developed to assist in positioning a saw used for the resection of the first metacarpal. Such cutting guides are positioned on the first metacarpal before resection thereof and are then withdrawn and so the possible locators which could have been provided with respect to the initial configuration of the patient's anatomy are lost.

Consequently, the surgeon must essentially operate "by sight" and must regularly take radiographs for verifying purposes in order to check that his various guides and tools are correctly positioned during the surgery. Furthermore, the trapeziometacarpal joint is specific to each patient and so the surgeon must systematically adapt his movements to the patient's anatomy. The placement of a trapeziometacarpal prosthesis is thus a delicate operation requiring much practice to be able to carry it out perfectly.

SUMMARY OF THE INVENTION

The present invention aims to propose a device for assisting in the placement of a trapeziometacarpal prosthesis, which permits the surgeon to position said prosthesis in an optimal manner according to the anatomy of his patient.

For this purpose, the present invention relates to a device for assisting in the placement of a trapeziometacarpal prosthesis comprising a cup intended to be fixed in the trapezium of a patient and a stem intended to be fixed in the patient's first metacarpal.

In accordance with the invention, said device comprises a first guide able to be interposed between the trapezium and the first metacarpal, said first guide comprising a first body having a first surface intended to be positioned on the articular surface of the trapezium, said first surface being congruent with said articular surface of the trapezium and a second surface intended to face the articular surface of the first metacarpal before resection. The first guide also comprises locating members carried by the first body and arranged to define resection lines for the first metacarpal.

Such a device for assisting in the placement of a trapeziometacarpal prosthesis permits reliable and precise positioning of the first guide in order to locate the resection lines for the first metacarpal in an optimal manner.

In a particularly advantageous manner, the assistance device can comprise a second guide arranged to be positioned on the first guide after resection of the first metacarpal, said second guide comprising a second body having a third surface intended to rest on the second surface of the first guide, and a fourth surface intended to face the resected first metacarpal, said third surface being congruent with the second surface of the first guide, and said second body of the second guide comprising, at least on its fourth surface, at least one guide orifice arranged to receive a tool.

The first body of the first guide preferably also comprises, at least on its second surface, at least one guide orifice arranged to receive a tool, the guide orifices being aligned, through-going and communicating.

Such a device for assisting in the placement of a trapeziometacarpal prosthesis permits reliable and precise positioning of a tool, such as a guide pin, required for placement of the prosthesis.

The present invention also relates to a method of producing such a device for assisting in the placement of a trapeziometacarpal prosthesis in which the first and second guides are produced pre-operatively specifically for a patient by 3D imaging.

BRIEF DESCRIPTION OF THE DRAWINGS

Other features and advantages of the present invention will become clear upon reading the following detailed description given with reference to the attached drawings in which.

DESCRIPTION OF THE PREFERRED EMBODIMENTS

Figure 1:
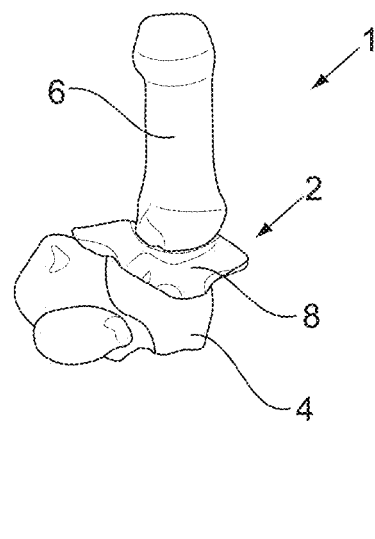
FIG. 1 is a perspective view of a first guide of an assistance device in accordance with the invention, interposed between the trapezium and the first metacarpal of a patient.
Figure 2:
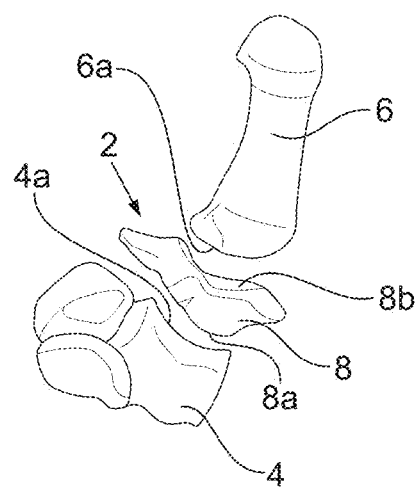
FIG. 2 is an exploded view of FIG. 1.
Figure 3:
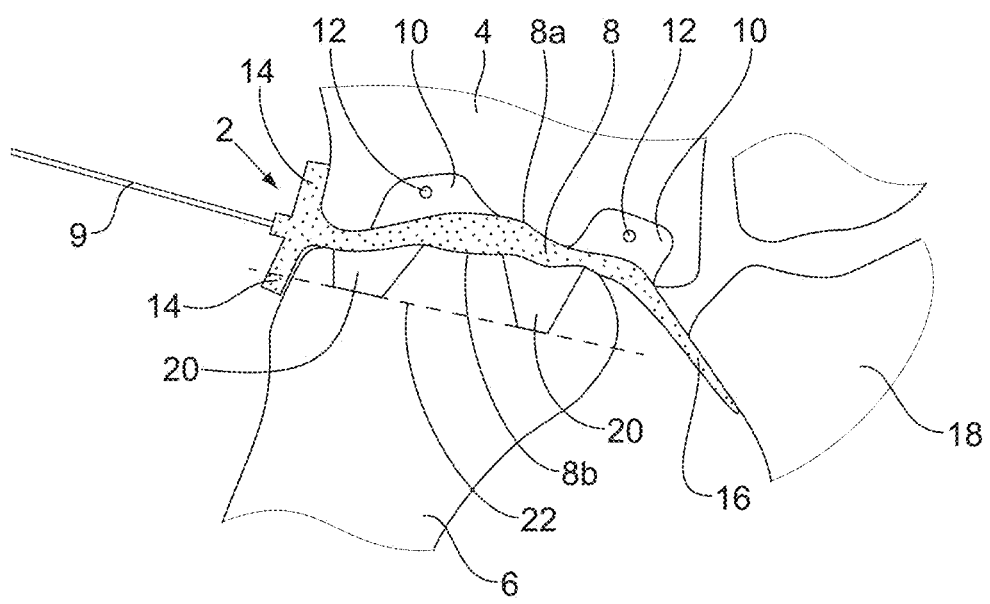
FIG. 3 is a top view of a first guide of an assistance device in accordance with the invention, interposed between the trapezium and the first metacarpal of a patient.

With reference to FIGS. 1 to 3, the device 1 for assisting in the placement of a trapeziometacarpal prosthesis in accordance with the invention comprises a first guide 2 able to be interposed between the trapezium 4 and the first metacarpal 6 of a patient. Said first guide 2 comprises a first body 8 having a first transverse surface 8*a* intended to be positioned on the saddle-shaped distal articular surface 4*a* of the trapezium 4, and more specifically intended to be positioned in contact with said distal articular surface 4*a*. For this purpose, said first surface 8*a* is congruent with the distal articular surface 4*a* of the trapezium 4 so that the two surfaces 8*a* and 4*a* perfectly match and fit together with each other. Opposite to the first surface 8*a* with respect to a transverse plane, the first body 8 of the first guide 2 has a second transverse surface 8*b* intended to face the proximal articular surface 6*a* of the first metacarpal 6 before resection. In a particularly preferred manner, the second surface 8*b* is able to be positioned in contact with the proximal articular surface 6*a*. For this purpose, and in a preferred manner, said second surface 8*b* is congruent with the proximal articular surface 6*a* of the first metacarpal 6 so that the two surfaces 8*b* and 6*a* perfectly match and fit together with each other.

The two surfaces 8*a* and 8*b* of the first body 8 of the first guide 2 being congruent with the articular surfaces of the trapezium 4 and of the first metacarpal 6 respectively, it is possible to interpose the first guide 2 between the trapezium 4 and the first metacarpal 6 in a stable and precise manner, and this is the case even if the articular surfaces 4*a*, 6*a* remaining available are small, according to the patient's anatomy or pathology. The congruency of the two opposing surfaces 8*a* and 8*b* of the first body 8 of the first guide 2 also permits space to be gained and thus access to be left for other tools or instruments required for the surgery.

The first guide 2 was produced at least partially, on an individualised basis with the aid of medical three-dimensional (3D) imaging at least of the trapezium 4 and of the first metacarpal 6 of the patient, pre-operatively, as will be detailed below. In particular, the configuration of the surfaces 8*a* and 8*b* was defined from a patient-specific virtual 3D model of the articular surfaces 4*a*, 6*a* of the trapezium 4 and of the first metacarpal 6 respectively in order that said surfaces 8*a* and 8*b* of the first body 8 are perfectly congruent with said articular surfaces 4*a* and 6*a* respectively.

A handle 9 can be provided at the outwardly directed end of the first guide 2 to facilitate manipulation thereof.

Although the stability of the first guide 2 between the trapezium 4 and the first metacarpal 6 is already ensured by its two congruent transverse surfaces 8*a*, 8*b* it is possible to provide, on the first guide 2, first fixing members arranged to become fixed on adjacent bones, in particular on the trapezium 4, to reinforce, at least temporarily, the holding of the first body 8 of the first guide 2 on said trapezium 4, in particular when the congruent surfaces 8*a*, 8*b* are small. These first fixing members can advantageously consist of fixing pads 10 or lugs protruding from the first body 8 over the dorsal face of the trapezium 4 and arranged to be fixed to the trapezium 4 (or other adjacent bone), e.g. by screws 12 screwed into corresponding holes provided for this purpose on the trapezium 4, or by any other suitable temporary fixing means.

Similarly, although the precise positioning of the first guide 2 between the trapezium 4 and the first metacarpal 6 is already ensured by its two congruent surfaces 8*a*, 8*b* it is possible to provide, on the first guide 2, positioning members arranged to guarantee precise interpositioning of the first body 8 of the first guide 2 between the trapezium 4 and the first metacarpal 6, in particular when the congruent surfaces 8*a*, 8*b* are small. These positioning members can advantageously comprise one or a plurality of centring pads 14 which are provided e.g. at the outwardly directed end of the first guide 2, between the handle 9 and the first guide 2, and are disposed substantially perpendicularly to the axis of the handle 9 on both sides of said handle 9. The centring pads 14 are positioned so as to come into abutment against the outer lateral faces of the trapezium 4 and of the first metacarpal 6 when the first body 8 is correctly interposed between the trapezium 4 and the first metacarpal 6.

The positioning members can also comprise one or a plurality of positioning pads 16 which are provided e.g. at the inwardly directed end of the first guide 2, which are disposed substantially as an extension of the first body 8 and are configured to come into abutment against the inner face of the trapezium 18 when the first body 8 is correctly interposed between the trapezium 4 and the first metacarpal 6.

The exact positioning of the fixing pads 10, of the centring pads 14 and of the positioning pads 16 on the first guide 2 is determined specifically for the patient by medical 3D imaging, pre-operatively, as detailed below.

Furthermore, the first guide 2 comprises locating members carried by the first body 8 and arranged to define resection lines 22 for the first metacarpal 6. These locating members can be integrated into the first guide 2 or be removable in order to be able to be withdrawn after the resection of the first metacarpal. More particularly, said locating members can be cutting pads 20, or lugs, forming a single piece with the first body 8 or being removable, protruding from the first body 8 of the first guide 2 over the dorsal face of the first metacarpal 6 and defining, by projection over said dorsal face of the first metacarpal 6, the resection lines 22 in a plane substantially perpendicular to the axis of the first metacarpal 6.

The exact positioning of the cutting pads 20 on the first guide 2 is determined specifically for the patient by medical 3D imaging, pre-operatively, as detailed below.

Figure 4:
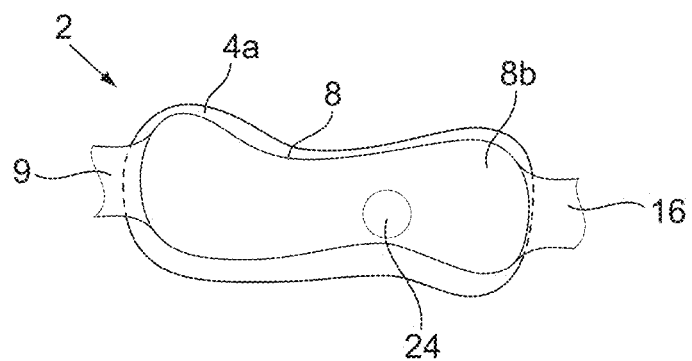
FIG. 4 is a front view of a trapezium carrying the first guide of an assistance device in accordance with the invention.

Furthermore, and with reference to FIG. 4, the first body 8 of the first guide 2 can comprise, at least on its second transverse surface 8*b*, at least one first guide orifice 24 arranged to receive a tool, after the resection of the base of the first metacarpal. This first guide orifice 24 is pre-operatively positioned and permits the surgeon at least to locate an entry point to position his tool, such as a guide pin, to prepare the trapezium.

In a particularly preferred manner, the first guide orifice 24 is a through-hole opening into the first transverse surface 8*a* to be able to reach the articular surface 4*a* of the lower face of the trapezium 4. The angle of inclination a of the first guide orifice 24 with respect to an axis substantially perpendicular to the articular surface 4*a* of the trapezium 4 is determined pre-operatively and permits the surgeon to orientate his tool, such as a guide pin, positioned in the first guide orifice 24 according to the correct angle of inclination.

Advantageously, the position as well as the angle of inclination a of the first guide orifice 24 of the first guide were defined pre-operatively in order to permit the placement of a tool, such as a guide pin, in the first guide 2 according to the best positioning and the best orientation possible with respect to the anatomy of the trapezium 4 and of the first metacarpal 6 of the patient.

Preferably, the exact positioning and angle of inclination of the first guide orifice 24 are determined specifically for the patient by medical 3D imaging, pre-operatively, as detailed below.

Figure 5:
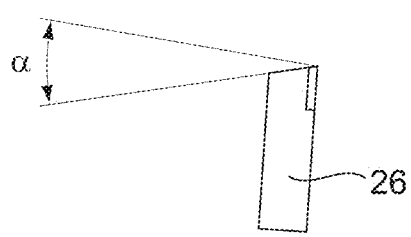
FIG. 5 is a front view of a drill bush used with the first guide illustrated in FIG. 4.

In order to improve the guidance of a tool positioned in the first guide orifice 24 after the resection of the first metacarpal, a drill bush 26, as illustrated in FIG. 5, can be provided, arranged to be introduced into the first guide orifice 24. The drill bush 26 has an end bevelled at the angle of inclination a in order to respect the angle of inclination determined for the first guide orifice 24. For safety reasons, a position-corrector corresponding to the drill bush 26 can be provided in the first guide orifice 24.

The addition of the drill bush 26 on the first guide 2 after the resection of the base of the first metacarpal permits improvement of the positioning and angle of inclination of a tool used to prepare the trapezium, such as a guide pin on which a drill such as a cannulated drill will be introduced.

Figure 6:
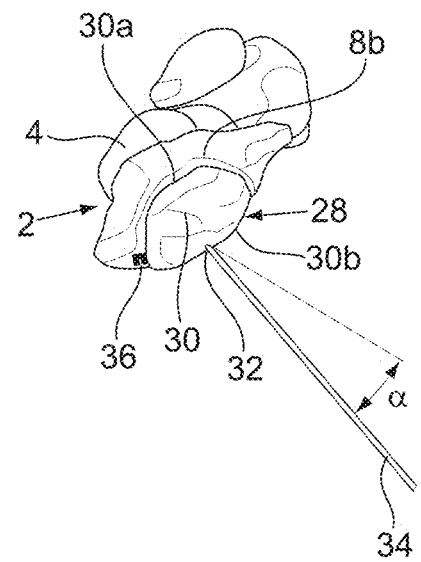
FIG. 6 is a perspective view of a first guide and of a second guide of an assistance device in accordance with the invention, which are positioned on the trapezium and have a guide pin passing through them.

According to a particularly preferred embodiment, and with reference to FIG. 6, the assistance device in accordance with the present invention further comprises a second guide 28 used instead of a drill bush 26. The second guide 28 is arranged to be positioned on the first guide 2 after resection of the base of the first metacarpal 6, and more specifically in contact with the second transverse surface 8*b* of the first guide 2. For this purpose, said second guide 28 comprises a second body 30 having a third transverse surface 30*a* intended to rest on the second transverse surface 8*b* of the first body 8 of the first guide 2, said third surface 30*a* being congruent with the second surface 8*b* of the first guide 2 so that the two surfaces 8*b* and 30*a* perfectly match and fit together with each other. In other words, the third surface 30*a* of the second guide 28 is identical to the articular surface 6*a* at the base of the first metacarpal 6. Opposite to the third transverse surface 30*a* with respect to a transverse plane, the second body 30 of the second guide 28 has a fourth transverse surface 30*b* intended to face the resected first metacarpal 6.

The surface 8*b* of the first body 8 of the first guide 2 and the surface 30*a* of the second body 30 of the second guide 28 being congruent, it is possible to position the second guide 28 on the first guide 2 in a stable and precise manner, and this is the case even if said surfaces 8*b* and 30 are small, according to the patient's anatomy or pathology. The congruency of the surface 8*b* of the first body 8 of the first guide 2 and of the surface 30*a* of the second body 30 of the second guide 28 also permit space to be gained.

The second guide 28 was produced at least partially on an individualised basis with the aid of medical three-dimensional (3D) imaging at least of the trapezium and of the first metacarpal of the patient, pre-operatively, as will be detailed below. In particular, the configuration of the surface 30*a* was defined from a patient-specific virtual 3D model of the articular surface 6*a* of the first metacarpal 6 in order that said surface 30*a* of the second body 30 is perfectly congruent with said articular surface 6*a* and consequently with the second surface 8*b* of the first guide 2.

Furthermore, the second body 30 of the second guide 28 comprises, at least on its fourth transverse surface 30*b*, at least one second guide orifice 32 arranged to receive a tool, after the resection of the base of the first metacarpal 6. This second guide orifice 32 is pre-operatively positioned and permits the surgeon at least to locate an entry point to position his tool, such as a guide pin 34, to prepare the trapezium.

In a particularly preferred manner, the second guide orifice 32 is a through-hole and is disposed so that the first guide orifice 24 and the second guide orifice 32 are throughgoing, aligned and communicating. Thus, the second guide orifice 32 passes through the second guide 28 to open into the second transverse surface 8*b* so that the articular surface 4*a* of the lower face of the trapezium 4 can then be reached by passing through the first guide orifice 24.

The fourth transverse surface 30*b* is configured so that the second guide 28 has a height sufficient to permit reliable guidance of a tool while permitting it to be inserted between the first guide 2 and the resected first metacarpal 6.

The angle of inclination a of the second guide orifice 32 with respect to an axis substantially perpendicular to the articular surface 4*a* of the trapezium 4 is the same as defined above. It is determined pre-operatively and permits the surgeon to orientate his tool, such as a guide pin 34, positioned in the second guide orifice 32 at the correct angle of inclination.

Advantageously, the position as well as the angle of inclination a of the second guide orifice 32 of the second guide 28 were defined pre-operatively in order to permit the placement of a tool, such as a guide pin 34, in the second guide 28 according to the best positioning and the best orientation possible with respect to the anatomy of the trapezium 4 and of the first metacarpal 6 of the patient.

Preferably, the exact positioning and angle of inclination of the second guide orifice 28 are determined specifically for the patient by medical 3D imaging, pre-operatively, as detailed below.

Although the stability of the second guide 28 on the first guide 2 is already ensured by their congruent surfaces 30*a* and 8*b* respectively, it is possible to provide, on the second guide 28, second fixing members 36, such as fixing lugs, arranged to at least temporarily hold the second body 30 of the second guide 28 on the first guide 2, in particular when the congruent surfaces 30*a*, 8*b* are small. The exact positioning of the second fixing members 36 on the second guide 28 is determined specifically for the patient by medical 3D imaging, pre-operatively, as detailed below.

The present invention also relates to a method of producing a device for assisting in the placement of a trapeziometacarpal prosthesis as described above, comprising the following steps:

a) producing, by medical imaging, a virtual model in three dimensions (3D) at least of the trapezium 4 and of the first metacarpal 6 of a patient, pre-operatively b) determining on the virtual 3D models obtained in step a) the best positioning and the best orientation possible for the placement of a tool in the trapezium 4 with respect to the anatomy of the trapezium 4 and of the first metacarpal 6 of the patient in view of the placement of the cup in the trapezium 4 and of the stem in the first metacarpal 6 c) determining, on the virtual 3D models obtained in step a), resection lines 22 for the first metacarpal 6 d) obtaining on the virtual 3D models obtained in step a) the articular surface 4*a* of the trapezium 4 and the articular surface 6*a* of the first metacarpal 6 e) creating a 3D image of the first and second guides 2, 28, the first transverse surface 8*a* of the first body 8 of the first guide 2 being configured to be congruent to the articular surface 4*a* of the trapezium 4 determined in step d), and the second transverse surface 8*b* of the first body 8 of the first guide 2 as well as the third transverse surface 30*a* of the second body 30 of the second guide 28 being configured to be congruent with each other, and preferably both to be congruent to the articular surface 6*a* of the first metacarpal 6 determined in step d)

f) determining the position of the locating members 20 on the 3D image of the first guide 2 created in step e) according to the resection lines 22 determined in step c)

g) determining the position of the first and second fixing members 10, 36 and of the positioning members 14, 16 on the 3D images of the first and second guides 2, 28 created in step e)

h) determining the position (entry point) and the angle of inclination a of the first and second guide orifices 24, 32 on the 3D images respectively of the first and second guides 2, 28 created in step e) according to the best positioning and the best orientation determined for the placement of a tool in step b)

i) producing the first and second guides 2, 28 according to the 3D images created in steps e) to h).

The medical imaging used in the present invention can be implemented using e.g. a CT scanner or any other suitable means. The virtual models of the trapezium and of the first metacarpal are reconstructed in 3D from the pre-operative CT scan images of the patient using digital modelling software such as computer-aided design (CAD) software or any other commercially available image processing software.

The first and second guides 2 and 28 are designed from virtual 3D models of the patient according to the process described above and are preferably produced according to step i) by 3D printing. It is obvious that any other known machining process could also be used. The first and second guides 2 and 28 are produced in materials compatible with 3D printers or with other machining processes as well as with the requirements of sterilisation. The materials for producing the first and second guides 2 and 28 can preferably be polyether ether ketone (PEEK), polypropylene, polyurethane, polyphenyl sulfone (PPSU), titanium-based alloys, stainless steels such as stainless steel 14021, or any other suitable material. Then the first and second guides 2 and 28 are sterilised in order then to be usable by the surgeon during the surgery.

During the surgery, after incision on the trapeziometacarpal joint and exposure of the first metacarpal 6, the first guide 2 is interposed between the trapezium 4 and the first metacarpal 6, then temporarily fixed to the trapezium by the fixing pads 10. By virtue of the surfaces 8a and 8b of the first guide 2 which are congruent with the articular surface 4a of the trapezium and the articular surface 6a of the first metacarpal 6 respectively, possibly assisted by the centring pads 14 and the positioning pads 16, which are specifically configured for the patient, the first guide 2 is interposed, in a stable, precise and patient-specific manner, between the articular surface 4a of the trapezium 4 and the articular surface 6a of the first metacarpal.

Then, the base of the first metacarpal 6 is resected following the resection lines 22 indicated by the cutting pads 20 or other locating member. The part of the resected first metacarpal is removed, which makes it possible to be able to move the first metacarpal slightly away from the trapezium. The medullary cavity can then be prepared to receive the stem in a manner known per se.

The second guide 28 is then interposed between the first guide 2 and the resected first metacarpal 6, then temporarily fixed to the first guide by the fixing lugs 36. By virtue of the surface 30a of the second guide 28 congruent with the second transverse surface 8b of the first guide 2, possibly assisted by the fixing lugs 36, which are configured specifically for the patient, the second guide 28 is interposed in a stable, precise and patient-specific manner, between the first guide 2 and the resected first metacarpal. The first guide 2 and the second guide 28 are fitted together so that the through-going first guide orifice 24 and the through-going second guide orifice 32 are aligned and communicating so as to constitute a guide path sufficiently long and precise to ensure and maintain optimal, patient-specific positioning and orientation of a guide pin 34 placed in said first and second guide orifices 24 and 32. After placement of the guide pin 34 in said first and second guide orifices 24 and 32, said guide pin 34 is introduced into the trapezium 4 using a motor. The first and second guides 2 and 28 are then withdrawn. Then a cannulated drill is introduced on the guide pin correctly positioned and orientated in the trapezium 4. The surgeon can then proceed to drill the trapezium for placement of the cup in the conventional manner. The guide pin 34 having remained in place in the trapezium 4 has the best positioning and the best orientation possible, defined according to the patient's anatomy pre-operation for the positioning of the trapeziometacarpal prosthesis.

The device for assisting in the placement of a trapeziometacarpal prosthesis in accordance with the invention makes it possible to propose both a cutting guide for the first metacarpal as well as a guide for positioning and orientation of a guide pin which are optimally configured specifically for the patient, requiring little space, which permits it to be able to be interposed in the small space of the trapeziometacarpal joint. The device for assisting in the placement of a trapeziometacarpal prosthesis in accordance with the invention can be positioned in a very precise and patient-specific manner on the trapeziometacarpal joint. It remains in place throughout the part of the surgery up to the placement of the correctly placed and orientated guide pin so that all the positioning locators of the trapeziometacarpal prosthesis which are defined according to the patient's anatomy pre-operation are preserved. The placement assistance device in accordance with the invention makes it possible to position a trapeziometacarpal prosthesis in an optimal manner, respecting the patient's anatomy.

The invention claimed is:

1. Device (1) for assisting in the placement of a trapeziometacarpal prosthesis comprising a cup intended to be fixed in the trapezium (4) of a patient and a stem intended to be fixed in the patient's first metacarpal (6), wherein said device comprises a first guide (2) able to be interposed between the trapezium (4) and the first metacarpal (6), said first guide (2) comprising a first body (8) having a first surface (8a) intended to be positioned on the articular surface (4a) of the trapezium (4), said first surface (8a) being congruent with said articular surface (4a) of the trapezium (4), and a second surface (8b) intended to face the articular surface (6a) of the first metacarpal (6) before resection, and locating members (20) carried by said first body (8) and arranged to define resection lines (22) for the first metacarpal (6).

2. Assistance device as claimed in claim 1, wherein the second surface (8b) of the first body (8) of the first guide (2) is congruent with the articular surface (6a) of the first metacarpal (6) so as to be suitable to be positioned on said articular surface (6a) of the first metacarpal (6) before resection.

3. Assistance device as claimed in claim 2, wherein the first guide (2) comprises first fixing members (10) arranged to reinforce the holding of the first body (8) of the first guide (2) on the trapezium (4).

4. Assistance device as claimed in claim 2, wherein the first guide (2) comprises positioning members (14, 16) arranged to guarantee the interpositioning of the first body (8) of the first guide (2) between the trapezium (4) and the first metacarpal (6).

5. Assistance device as claimed in claim 2, further comprising a second guide (28) arranged to be positioned on the first guide (2) after resection of the first metacarpal (6), said second guide (28) comprising a second body (30) having a third surface (30a) intended to rest on the second surface (8b) of the first guide (2), and a fourth surface (30b) intended to face the resected first metacarpal (6), said third surface (30a) being congruent with the second surface (8b) of the first guide (2), and wherein said second body (30) of the second guide (28) comprises, at least on its fourth surface (30b), at least one second guide orifice (32) arranged to receive a tool (34).

6. Assistance device as claimed in claim 1, wherein the first guide (2) comprises first fixing members (10) arranged to reinforce the holding of the first body (8) of the first guide (2) on the trapezium (4).

7. Assistance device as claimed in claim 6, wherein the first guide (2) comprises positioning members (14, 16) arranged to guarantee the interpositioning of the first body (8) of the first guide (2) between the trapezium (4) and the first metacarpal (6).

8. Assistance device as claimed in claim 6, further comprising a second guide (28) arranged to be positioned on the first guide (2) after resection of the first metacarpal (6), said second guide (28) comprising a second body (30) having a third surface (30a) intended to rest on the second surface (8b) of the first guide (2), and a fourth surface (30b) intended to face the resected first metacarpal (6), said third surface (30a) being congruent with the second surface (8b) of the first guide (2), and wherein said second body (30) of the second guide (28) comprises, at least on its fourth surface (30b), at least one second guide orifice (32) arranged to receive a tool (34).

9. Assistance device as claimed in claim 1, wherein the first guide (2) comprises positioning members (14, 16) arranged to guarantee the interpositioning of the first body (8) of the first guide (2) between the trapezium (4) and the first metacarpal (6).

10. Assistance device as claimed in claim 1, wherein the first body (8) of the first guide (2) comprises, at least on its second surface (8b), at least one first guide orifice (24) arranged to receive a tool (34).

11. Assistance device as claimed in claim 10, further comprising a second guide (28) arranged to be positioned on the first guide (2) after resection of the first metacarpal (6), said second guide (28) comprising a second body (30) having a third surface (30a) intended to rest on the second surface (8b) of the first guide (2), and a fourth surface (30b) intended to face the resected first metacarpal (6), said third surface (30a) being congruent with the second surface (8b) of the first guide (2), and wherein said second body (30) of the second guide (28) comprises, at least on its fourth surface (30b), at least one second guide orifice (32) arranged to receive a tool (34).

12. Device as claimed in claim 11, wherein the first and second guide orifices (24, 32) are aligned, through-going and communicating.

13. Assistance device as claimed in claim 11, wherein the second guide (28) comprises second fixing members (36) arranged to hold the second body (30) of the second guide (28) on the first guide (2).

14. Assistance device as claimed in claim 11, wherein the second guide (28) was produced at least partially on an individualised basis with the aid of medical three-dimensional (3D) imaging at least of the trapezium (4) and of the first metacarpal (6) of the patient, pre-operatively.

15. Assistance device as claimed in claim 14, wherein the position and the inclination of the second guide orifice (32) of the second guide (28) were defined pre-operatively in order to permit the placement of a tool (34) in the second guide (28) according to the best positioning and the best orientation possible with respect to the anatomy of the trapezium (4) and of the first metacarpal (6) of the patient.

16. Assistance device as claimed in claim 1, wherein the first guide (2) was produced at least partially on an individualised basis with the aid of medical three-dimensional (3D) imaging at least of the trapezium (4) and of the first metacarpal (6) of the patient, pre-operatively.

17. Assistance device as claimed in claim 16, wherein the position and the inclination of the first guide orifice (24) of the first guide (2) were defined pre-operatively in order to permit the placement of a tool (34) in the first guide (2) according to the best positioning and the best orientation possible with respect to the anatomy of the trapezium (4) and of the first metacarpal (6) of the patient.

18. Method of producing a device for assisting in the placement of a trapeziometacarpal prosthesis according to claim 1, comprising the following steps:
a) producing, by medical imaging, a virtual model in three dimensions (3D) at least of the trapezium (4) and of the first metacarpal (6) of a patient, pre-operatively
b) determining on the virtual 3D models obtained in step a) the best positioning and the best orientation possible for the placement of a tool (34) in the trapezium (4) with respect to the anatomy of the trapezium (4) and of the first metacarpal (6) of the patient
c) determining, on the virtual 3D models obtained in step a), resection lines (22) for the first metacarpal (6)
d) obtaining on the virtual 3D models obtained in step a) the articular surface (4a) of the trapezium (4) and the articular surface (6a) of the first metacarpal (6)
e) creating a 3D image of the first and second guides (2, 28), the first surface (8a) of the first guide (2) being configured to be congruent to the articular surface (4a) of the trapezium (4) determined in step d), and the second surface (8b) of the first guide (2) as well as the third surface (30a) of the second guide (28) being configured to be congruent with each other
f) determining the position of the locating members (20) on the 3D image of the first guide (2) created in step e) according to the resection lines (22) determined in step c)
g) determining the position of the first and second fixing members (10, 36) and of the positioning members (14, 16) on the 3D images of the first and second guides (2, 28) created in step e)
h) determining the position of the first and second guide orifices (24, 32) on the 3D images respectively of the first and second guides (2, 28) created in step e) according to the best positioning and the best orientation determined for the placement of a tool (34) in step b)
i) producing the first and second guides (2, 28) according to the 3D images created in steps e) to h).

19. Method of producing a device for assisting in the placement of a trapeziometacarpal prosthesis as claimed in claim 18, wherein the second surface (8b) of the first guide (2) configured in step e) is configured to be congruent with the articular surface (6a) of the first metacarpal (6) determined in step d).

20. Assistance device as claimed in claim 1, further comprising a second guide (28) arranged to be positioned on the first guide (2) after resection of the first metacarpal (6), said second guide (28) comprising a second body (30) having a third surface (30a) intended to rest on the second surface (8b) of the first guide (2), and a fourth surface (30b)

intended to face the resected first metacarpal (6), said third surface (30*a*) being congruent with the second surface (8*b*) of the first guide (2), and wherein said second body (30) of the second guide (28) comprises, at least on its fourth surface (30*b*), at least one second guide orifice (32) arranged to receive a tool (34).

\* \* \* \* \*